(12) United States Patent
Paek et al.

(10) Patent No.: US 11,738,057 B2
(45) Date of Patent: Aug. 29, 2023

(54) LACTOBACILLUS HAVING BLOOD GLUCOSE LOWERING EFFECT AND ANTIOXIDANT EFFECT

(71) Applicants: MEDIOGEN CO., LTD., Chungcheongbuk-do (KR); Nam-Soo Paek, Seoul (KR)

(72) Inventors: Nam-Soo Paek, Seoul (KR); Chang Ho Kang, Chungcheongbuk-do (KR)

(73) Assignee: Mediogen Co., Ltd., Chungcheongbuk-do (KR)

( * ) Notice: Subject to any disclaimer, the term of this patent is extended or adjusted under 35 U.S.C. 154(b) by 185 days.

(21) Appl. No.: 16/936,211

(22) Filed: Jul. 22, 2020

(65) Prior Publication Data
US 2021/0023147 A1    Jan. 28, 2021

(30) Foreign Application Priority Data
Jul. 23, 2019 (KR) .................. 10-2019-0088795

(51) Int. Cl.
| | | |
|---|---|---|
| *A61K 39/02* | (2006.01) | |
| *A01N 63/00* | (2020.01) | |
| *A61K 35/747* | (2015.01) | |
| *A61P 3/10* | (2006.01) | |
| *A61K 35/00* | (2006.01) | |

(52) U.S. Cl.
CPC .............. *A61K 35/747* (2013.01); *A61P 3/10* (2018.01); *A61K 2035/115* (2013.01)

(58) Field of Classification Search
None
See application file for complete search history.

(56) References Cited

U.S. PATENT DOCUMENTS

2012/0195868 A1* 8/2012 Lathan ...................... A61P 1/00
                                                                    426/61
2021/0187044 A1* 6/2021 Kim ...................... A61K 35/747

FOREIGN PATENT DOCUMENTS

WO      2002/38165 A1 *  5/2002
WO      2017/204374 A1 * 11/2017

* cited by examiner

*Primary Examiner* — Jennifer E Graser
(74) *Attorney, Agent, or Firm* — Myers Bigel, P.A.

(57) ABSTRACT

Disclosed is a *Lactobacillus* strain having a blood glucose lowering effect and an antioxidant effect, a culture medium of the strain, and a cell-free supernatant of the strain. Further, a composition for lowering a blood glucose level contains the same. A composition having an antioxidant ability contains the same. The *Lactobacillus plantarum* MG4229 strain according to the present disclosure has excellent blood glucose lowering activity and antioxidant activity, and has excellent acid tolerance, bile tolerance, auto-aggregation, and adhesion to epithelial cells, and thus is suitable for probiotics, and thus may be used in various ways as a composition for preventing or treating diabetes mellitus or a composition having antioxidant ability.

13 Claims, 2 Drawing Sheets

Specification includes a Sequence Listing.

SEQUENCE LISTING

```
<160> NUMBER OF SEQ ID NOS: 1

<210> SEQ ID NO 1
<211> LENGTH: 1438
<212> TYPE: DNA
<213> ORGANISM: Artificial
<220> FEATURE:
<223> OTHER INFORMATION: Lactobacillus plantarum MG4229

<400> SEQUENCE: 1
tgcagtcgaa cgaactctgg tattgattgg tgcttgcatc atgatttaca tttgagtgag      60
tggcgaactg gtgagtaaca cgtgggaaac ctgcccagaa gcgggggata acacctggaa     120
acagatgcta ataccgcata acaacttgga ccgcatggtc cgagcttgaa agatggcttc     180
ggctatcact tttggatggt cccgcggcgt attagctaga tggtggggta acggctcacc     240
atggcaatga tacgtagccg acctgagagg gtaatcggcc acattgggac tgagacacgg     300
cccaaactcc tacgggaggc agcagtaggg aatcttccac aatggacgaa agtctgatgg     360
agcaacgccg cgtgagtgaa gaagggtttc ggctcgtaaa actctgttgt taaagaagaa     420
catatctgag agtaactgtt caggtattga cggtatttaa ccagaaagcc acggctaact     480
acgtgccagc agccgcggta atacgtaggt ggcaagcgtt gtccggattt attgggcgta     540
aagcgagcgc aggcggtttt ttaagtctga tgtgaaagcc ttcggctcaa ccgaagaagt     600
gcatcggaaa ctgggaaact tgagtgcaga agaggacagt ggaactccat gtgtagcggt     660
gaaatgcgta gatatatgga agaacaccag tggcgaaggc ggctgtctgg tctgtaactg     720
acgctgaggc tcgaaagtat gggtagcaaa caggattaga taccctggta gtccataccg     780
```

-continued

```
taaacgatga atgctaagtg ttggagggtt tccgcccttc agtgctgcag ctaacgcatt    840
aagcattccg cctggggagt acggccgcaa ggctgaaact caaaggaatt gacgggggcc    900
cgcacaagcg gtggagcatg tggtttaatt cgaagctacg cgaagaacct taccaggtct    960
tgacatacta tgcaaatcta agagattaga cgttcccttc ggggacatgg atacaggtgg   1020
tgcatggttg tcgtcagctc gtgtcgtgag atgttgggtt aagtcccgca acgagcgcaa   1080
cccttattat cagttgccag cattaagttg ggcactctgg tgagactgcc ggtgacaaac   1140
cggaggaagg tggggatgac gtcaaatcat catgcccctt atgacctggg ctacacacgt   1200
gctacaatgg atggtacaac gagttgcgaa ctcgcgagag taagctaatc tcttaaagcc   1260
attctcagtt cggattgtag gctgcaactc gcctacatga agtcggaatc gctagtaatc   1320
gcggatcagc atgccgcggt gaatacgttc ccgggccttg tacacaccgc ccgtcacacc   1380
atgagagttt gtaacaccca aagtcggtgg ggtaaccttt taggaaccag ccgcctaa    1438
```

LACTOBACILLUS HAVING BLOOD GLUCOSE LOWERING EFFECT AND ANTIOXIDANT EFFECT

CROSS-REFERENCE TO RELATED APPLICATIONS

This application is based on and claims priority from Korean Patent Application No. 10-2019-0088795, filed on Jul. 23, 2019 with the Korean Intellectual Property Office, the disclosure of which is incorporated herein in its entirety by reference.

STATEMENT REGARDING ELECTRONIC FILING OF A SEQUENCE LISTING

A Sequence Listing in ASCII text format, submitted under 37 C.F.R. § 1.821, entitled 1547-5_ST25.txt, 2,336 bytes in size, generated on Jul. 14, 2020 and filed via EFS-Web, is provided in lieu of a paper copy. This Sequence Listing is hereby incorporated by reference into the specification for its disclosures.

FIELD OF THE INVENTION

The present disclosure relates to a *Lactobacillus* strain having a blood glucose lowering effect and an antioxidant effect, a culture medium of the strain, and a cell-free supernatant of the strain, and relates to a composition for lowering a blood glucose level containing the same, and a composition having an antioxidant ability containing the same.

BACKGROUND OF THE INVENTION

Due to westernized diet and lack of exercise, incidence of various adult diseases related to a lifestyle is increasing. In particular, changes in diet cause changes in microbiota of a human digestive tract. This increases endotoxin produced by the microbiota in the digestive tract. When the endotoxin increases in the digestive tract, inflammation of the digestive tract is induced, absorption of the endotoxin into a body increases, and movement of macrophages to an adipose tissue is promoted, leading to obesity or hyperglycemia. Therefore, controlling the endotoxin produced by the microbiota of the digestive tract allows a blood glucose level to be controlled. Thus, ultimately, this improves or cures diabetes mellitus.

Diabetes mellitus is a typical chronic disease and is a chronic disease that causes microvascular complications of retina, kidney and nerve, and large vessel complications such as paralysis, angina, myocardial infarction and peripheral vascular disease, due to various metabolic disorders including glucose metabolic disorders. Drug therapy for blood glucose control uses insulin and chemicals, such that side effects of drug use and patient chemical resistance are constantly becoming a problem.

The diabetes mellitus is a metabolic disorder caused by impaired secretion and lack of action of insulin as secreted by pancreatic cells. This entails overproduction of glucose, decomposition of body fat and waste of protein and abnormally promotes glucagon secretion, thus causing metabolic disruption. In the diabetes mellitus, hormone imbalance including insulin imbalance causes abnormal physiological metabolic regulation functions related to metabolism of protein, lipid and electrolyte, carbohydrate, thereby to cause characteristic symptoms of hyperglycemia. When these hyperglycemia symptoms persist, this causes blood circulation disorders, retinal damage, nerve cell damage, kidney function decline, and vascular complications.

There are two major types of diabetes mellitus, namely, type 1 diabetes mellitus and type 2 diabetes mellitus. Type 1 diabetes mellitus is caused by a lack of secretion of insulin as a glucose-regulating hormone in the blood, and usually occurs in young people in their 10s and 20s. Type 2 diabetes mellitus usually develops after age 40 and accounts for the majority of patients of the diabetes mellitus. As an etiology of type 2 diabetes mellitus, both impairment of insulin secretion in pancreatic beta cells and insulin action defects (insulin resistance) in target cells are observed. Insulin resistance refers to a state in which insulin action is reduced in peripheral tissues and is a major cause of type 2 diabetes mellitus.

The most important goal in treatment of diabetes mellitus is to control blood glucose level as close to normal as possible. Drug therapy, diet and exercise therapy are the treatment methods thereof. Current oral hypoglycemic agents used in patients with diabetes mellitus include α-glucosidase inhibitors, sulfonylurea preparations and biguanide preparations. The α-glucosidase inhibitor shows a therapeutic effect of diabetes mellitus by delaying digestion and absorption of carbohydrates in an ingested diet, thereby reducing post-prandial blood glucose and blood insulin level. The α-glucosidase inhibitors do not cause hyperinsulinemia or hypoglycemia, and has an advantage of promoting secretion in a small intestine of glucagon-like-peptide-1 which promotes insulin secretion and inhibits glucagon secretion.

The α-glucosidase inhibitors as currently used in clinical trials include acarbose, voglibose and miglitol. However, long-term use of the α-glucosidase inhibitors may cause side effects such as bloating, vomiting, or diarrhea in some patients, and thus their use may be limited.

Further, in addition to diabetes, aging is an important health problem in an aging society. A process of aging is influenced by complex effects of genetics, environment, and lifestyle. Various morphological and biochemical changes are involved in the aging process. In particular, an increase in oxidative stress and an increase in inflammatory response are considered to be main causes involved in promoting the aging. Oxidative stress occurs due to increased production of reactive oxygen species (ROS) or a decrease in an antioxidant defense mechanism in the body. As a result, biopolymers, such as DNA, are destroyed and cell damage is caused to accelerate the aging, and to increase a risk of aging disease such as neurodegenerative diseases including dementia, cancers, and cardiovascular diseases.

Accordingly, as the society progresses to an aging society, development of substances that prevent or treat hyperlipidemia, the diabetes mellitus, hypertension, etc. using natural products that are dietary and have fewer side effects is required. Further, a substance having antioxidant activity is required to prevent aging.

SUMMARY OF THE INVENTION

Thus, the present inventors have conducted researching of probiotics to prevent a risk of diabetes mellitus from occurring and recurring and to be used as an alternative to drugs currently used to treat diabetes mellitus. As a result, among lactic acid bacteria (LAB), lactic acid bacteria (LAB) strains possessing excellent α-glucosidase inhibitory effect and having excellent antioxidant activity were selected and characteristics thereof were identified. Based on the identification result, we have obtained a lactic acid bacteria (LAB) strain having high antioxidant activity and high blood glucose control ability. In this manner, the present disclosure was completed.

Therefore, the present disclosure has been made in an effort to provide a lactic acid bacteria (LAB) strain, that is, *Lactobacillus* strain having blood glucose lowering activity, a culture medium of the strain, and a cell-free supernatant of the strain.

Further, the present disclosure has been made in an effort to provide a composition for lowering a blood glucose level, the composition containing the strain, the culture medium thereof, or the supernatant thereof.

Further, the present disclosure has been made in an effort to provide a composition for preventing or ameliorating diabetes mellitus, the composition containing the strain, the culture medium thereof, or the supernatant thereof.

Further, the present disclosure has been made in an effort to provide a composition having an antioxidant ability, the composition containing the strain, the culture medium thereof, or the supernatant thereof.

An exemplary embodiment of the present disclosure provides *Lactobacillus plantarum* MG4229 strain with blood glucose lowering activity and antioxidant activity.

Further, another exemplary embodiment of the present disclosure provides a first composition containing at least one kind selected from the group consisting of the strain, the culture medium of the strain, and the cell-free supernatant of the strain.

Further, yet another exemplary embodiment of the present disclosure provides a health functional food composition for lowering blood glucose level, the health functional food composition containing the first composition.

Further, yet another exemplary embodiment of the present disclosure provides a pharmaceutical composition for preventing or treating diabetes mellitus, the pharmaceutical composition containing the first composition.

Further, yet another exemplary embodiment of the present disclosure provides a health functional food composition for preventing or ameliorating diabetes mellitus, the health functional food composition containing the first composition.

Further, yet another exemplary embodiment of the present disclosure provides a quasi-drug composition for preventing or ameliorating diabetes mellitus, the quasi-drug composition containing the first composition.

Further, yet another exemplary embodiment of the present disclosure provides a health functional food composition with an antioxidant ability, the health functional food composition containing the first composition.

According to the exemplary embodiments of the present disclosure, the *Lactobacillus plantarum* MG4229 strain according to the present disclosure has excellent blood glucose lowering activity and antioxidant activity and has excellent acid tolerance, bile tolerance, auto-aggregation ability and adhesion to epithelial cell, and thus is suitable for probiotics. Thus, the *Lactobacillus plantarum* MG4229 strain according to the present disclosure may be used in various ways as a composition for preventing or treating diabetes mellitus or a composition having antioxidant ability.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The present disclosure provides *Lactobacillus plantarum* MG4229 strain having blood glucose lowering activity and antioxidant activity.

The *Lactobacillus plantarum* MG4229 strain according to the present disclosure has excellent blood glucose lowering activity based on excellent α-glucosidase inhibitory activity, α-amylase inhibitory activity, and insulin resistance improvement effect, and has high DPPH radical scavenging ability and ABTS radical scavenging ability, and thus exhibits excellent antioxidant activity. Further, the *plantarum* MG4229 strain according to the present disclosure has excellent acid tolerance, bile tolerance, auto-aggregation and adhesion to epithelial cells in an intestine.

Hereinafter, the present disclosure will be described in detail.

The *Lactobacillus plantarum* MG4229 strain is a strain having blood glucose lowering activity and antioxidant activity.

In the present disclosure, the term "blood glucose lowering activity" refers to an effect of lowering a blood glucose level as a measure of a glucose concentration in the blood. It is desirable for a human body to maintain the blood glucose level within a certain range in order to maintain homeostasis. A hyperglycemia refers to an abnormally high blood glucose level. The hyperglycemia that appears temporarily after eating is a natural phenomenon and is called a physiological hyperglycemia. However, an increased blood glucose level or a continued hyperglycemic condition beyond this range may result in diabetes, and may be likely to progress to diabetes. In this connection, the diabetes is onset, but is likely to be undiscovered. According to regulations of the US Food and Drug Administration, a normal blood glucose level is defined as fasting blood glucose of less than 100 mg/dl and blood glucose of 2 hours after eating less than 140 mg/dl. Diabetes mellitus is diagnosed when the fasting blood glucose of 126 mg/dl or higher and blood glucose of 2 hours after meals of 200 mg/dl or higher are observed. Meanwhile, WHO defines fasting blood glucose of less than 110 mg/dl as a normal level. Although a current blood glucose level is below the level at which the diabetes mellitus is diagnosed, a hyperglycemic condition beyond a normal state may continue. This may cause fatty liver and increase a risk of progressing to severe liver disease and cause cardiovascular disease and complications thereof. In the body, glucagon, adrenaline, insulin, and thyroid hormones act to maintain the normal blood glucose level. When abnormalities occur in the secretion and/or activity of these hormones, hyperglycemia may occur. Moreover, excessive sugar intake, lack of exercise and/or stress may cause hyperglycemia. The *Lactobacillus plantarum* MG4229 strain according to the present disclosure may exhibit blood glucose lowering effect based on α-glucosidase inhibitory activity, α-amylase inhibitory activity and insulin resistance improvement effect, and thus may have prevention and improvement effect on diseases caused by the hyperglycemia.

In the present disclosure, the term "antioxidant activity" may be an antioxidant action. Oxidation of biolipids by active oxygens may cause damages to proteins (which contain various enzymes) or DNA which is responsible for genetic information, in addition to a bio-membrane phospholipid (containing an unsaturated fatty acid). Furthermore, diseases such as liver disorders, circulatory system diseases or cancer, and aging may be induced. The *Lactobacillus plantarum* MG4229 strain according to the present disclosure may inhibit the activity induced by the active oxygens, based on the antioxidant activity.

In the present disclosure, the term "*Lactobacillus*" refers to a bacterium that generates a large amount of lactic acid by obtaining energy by fermenting sugars widely distributed in nature. The *Lactobacillus* is a morphologically gram-positive asporogenous bacillus, and is morphologically polymorphic. The *Lactobacillus plantarum* MG4229 strain according to the present disclosure having excellent blood glucose lowering activity, excellent acid tolerance, bile tolerance, auto-aggregation, and adhesion to epithelial cells was deposited with the Korea Research Institute of Bioscience and Biotechnology on Jun. 4, 2019, and was assigned a deposit number KCTC13854BP. The present inventors have identified the *Lactobacillus plantarum* MG4229 strain as follows.

In order to isolate the *Lactobacillus* strain according to the present disclosure, we have selected and identified strains with excellent blood glucose lowering activity and antioxidant activity among the 237 types of lactic acid bacteria (LAB) strains. Then, the selected and identified strains with the excellent blood glucose lowering activity and antioxidant activity was the *Lactobacillus plantarum* MG4229 strain.

The *Lactobacillus plantarum* MG4229 strain according to the present disclosure has excellent blood glucose lowering activity.

The *Lactobacillus plantarum* MG4229 strain according to the present disclosure has excellent α-glucosidase inhibitory activity.

When the activity of α-glucosidase is inhibited, digestion and absorption of sugars may be delayed, which may lower increased blood glucose after eating.

The *Lactobacillus plantarum* MG4229 strain according to the present disclosure has excellent α-amylase inhibitory activity.

When the activity of α-amylase is inhibited, digestion of starch in a small intestine may be inhibited, and absorption of glucose may be delayed, thereby lowering hyperglycemia.

The *Lactobacillus plantarum* MG4229 strain according to the present disclosure has an excellent effect of improving insulin resistance.

The *Lactobacillus plantarum* MG4229 strain according to the present disclosure has excellent antioxidant activity.

According to the present disclosure, the antioxidant activity may be measured based on a DPPH scavenging ability and an ABTS scavenging ability. The *Lactobacillus plantarum* MG4229 strain according to the present disclosure may have excellent DPPH scavenging ability and ABTS scavenging ability.

The *Lactobacillus plantarum* MG4229 strain according to the present disclosure may exhibit the antioxidant activity to inhibit damages to phospholipids, proteins, nucleic acids, etc. in vivo by active oxygen, and to prevent the aging.

The strain according to the present disclosure may have acid tolerance, and, may be preferably stable at pH 2 to 7. More preferably, the strain according to the present disclosure may be stable in a body gastric fluid condition of pH 2 to 7 for a gastric emptying time of 2 to 3 hours.

Moreover, the strain according to the present disclosure may have bile tolerance. Preferably, the strain according to the present disclosure may be stable in a bile salt. More preferably, the strain according to the present disclosure may be stable at 0.1 to 1% bile salt, even more preferably, at 0.1 to 0.5% bile salt.

The *Lactobacillus plantarum* MG4229 strain according to the present disclosure has excellent auto-aggregation, and high hydrophobicity relative to a cell surface, and high adhesion to epithelial cells. Therefore, the *Lactobacillus plantarum* MG4229 strain according to the present disclosure may prevent removal of probiotics via an enterospasm motion and may effectively form colonies on epithelial cells in the intestine and thus settle well on the intestine. The adhesion to the cells may be effective in maintaining an effect of the probiotics.

The hydrophobicity to the cell surface means presence of proteins on the cell surface. A hydrophilicity to the cell surface means presence of many polysaccharides on the cell surface. The more the proteins on the cell surface, the better the auto-aggregation and the adhesion to the cells. The *Lactobacillus plantarum* MG4229 strain according to the present disclosure may have high adhesion to xylene and may exhibit hydrophobicity to the cell surface and may have excellent auto-aggregation and adhesion to the cells.

The *Lactobacillus plantarum* MG4229 strain according to the present disclosure may be resistant to antibiotics including vancomycin, kanamycin, and clindamycin. The *Lactobacillus plantarum* MG4229 strain according to the present disclosure may exhibit antibiotic susceptibility to antibiotics including ampicillin, gentamycin, streptomycin, tetracyclin, erythromycin, and chloramphenicol.

The *Lactobacillus plantarum* MG4229 strain according to the present disclosure may induce enzyme activity of esterase (C4), esterase lipase (C8), lipase (14), leucine arylamidase, valine arylamidase, crystinearylamidase, trypsin, α-chymotrypsin, acid phosphatase, naphtol-AS-BI-phosphohydrolase, α-galactosidase, β-glucuronidase, β-glucosidase, n-acetyl-β-glucosaminidase, or α-mannosidase.

The *Lactobacillus plantarum* MG4229 strain according to the present disclosure may exhibit fermentation characteristics of L-arabinose, D-ribose, D-galactose, D-glucose, D-fructose, D-mannose, mannitol, D-sorbitol, methyl α D-mannopyranoside, N-acetylglucosamine, amygdalin, arbutin, esculin, salicin, D-cellobiose, D-maltose, D-lactose, D-melibiose, D-saccharose, D-trehalose, D-melezitose, D-raffinose, gentibiose, D-turanose, or potassium gluconate.

Further, the present disclosure provides a first composition containing at least one kind selected from the group consisting of the strain, a culture medium of the strain, and a cell-free supernatant of the strain.

The first composition according to the present disclosure may further contain additional ingredients such as pharmaceutically acceptable or nutritionally acceptable carriers, excipients or diluents.

The first composition according to the present disclosure may be used for the purpose of lowering a blood glucose level, and further, for prevention, treatment, improvement or delay of onset of diabetes mellitus. In this connection, diabetes mellitus is meant to include insulin-dependent diabetes mellitus (type 1 diabetes mellitus) and insulin-independent diabetes mellitus (type 2 diabetes mellitus). Furthermore, diabetes mellitus includes diabetes mellitus that occurs when the pancreas is damaged due to other diseases, such as diabetes mellitus caused by hyperthyroidism, hypoadreno corticism, excess secretion of growth hormone or catecholamines, or gestational diabetes mellitus.

The first composition according to the present disclosure may exhibit the antioxidant activity, thereby inhibiting damages to bio-membrane phospholipids, proteins or nucleic acids, etc. by active oxygen and to achieve anti-aging of cells.

The first composition according to the present disclosure may contain the active ingredient in an effective dose according to uses, formulations, combination purposes, etc. as long as it may exhibit hypoglycemic activity or antioxidant activity. A typical effective dose will be determined in a range of 0.001% to 99.990% by weight, based on a total weight of the composition. In this connection, the "effective dose" refers to an amount of the active ingredient that may induce hypoglycemic activity or antioxidant activity. This effective dose may be determined empirically by the skilled person to the art. The subjects to which the composition according to the present disclosure may be applied (administered) are mammals and humans. Particularly, the subject is preferable a human.

Further, the present disclosure provides a health functional food composition for lowering a blood glucose level, the composition containing the above first composition.

Further, the present disclosure provides a pharmaceutical composition for preventing or treating diabetes mellitus, the composition containing the above first composition.

Further, the present disclosure provides a health functional food composition for preventing or ameliorating diabetes mellitus, the composition containing the above first composition.

Further, the present disclosure provides a quasi-drug composition for preventing or ameliorating diabetes mellitus, the composition containing the above first composition.

Further, the present disclosure provides a health functional food composition having an antioxidant ability, the composition containing the above first composition.

In the present disclosure, the term 'prevention' may mean any action that suppresses or delays onset of diabetes mellitus by administering the composition according to the present disclosure to an individual.

In the present disclosure, the term 'treatment' may mean any action that reduces symptoms of diabetes mellitus or is beneficial, by administering the composition according to the present disclosure to a subject suspected of having diabetes mellitus.

The health functional food composition for lowering the blood glucose level, the pharmaceutical composition for preventing or treating diabetes mellitus, the health functional food composition for preventing or ameliorating diabetes mellitus, the quasi-drug composition for preventing or ameliorating diabetes mellitus, and the health functional food composition having the antioxidant ability may contain the strain, the culture medium thereof or the cell-free supernatant thereof alone as an active ingredient, or may further contain additional ingredients such as pharmaceutically acceptable or nutritionally acceptable carriers, excipients, diluents or auxiliary ingredients, depending on a formulation thereof, a method of use and a purpose of use thereof.

More specifically, the health functional food composition for lowering the blood glucose level, the pharmaceutical composition for preventing or treating diabetes mellitus, the health functional food composition for preventing or ameliorating diabetes mellitus, the quasi-drug composition for preventing or ameliorating diabetes mellitus, and the health functional food composition having the antioxidant ability may further contain, in addition to the active ingredient, nutrients, vitamins, electrolytes, flavoring agents, colorants, neutralizers, pectic acid and salts thereof, alginic acid and salts thereof, organic acids, a protective colloidal thickener, a pH adjusting agent, a stabilizer, preservative, glycerin, alcohol, carbonic acid used in carbonated beverages, and the like.

Further, the carrier, excipient or diluent may be one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil, dextrin, calcium carbonate, propylene glycol, liquid paraffin, and physiological saline. However, the present disclosure is not limited thereto. Any common carrier, excipient, or diluent may be used. The above additive ingredients may be added to the pharmaceutical composition as the active ingredient independently or in combination with each other.

Further, the pharmaceutical composition for preventing or treating diabetes mellitus may further contain a conventional filler, bulking agent, binder, disintegrant, surfactant, anticoagulant, lubricant, wetting agent, fragrance, emulsifier or preservative. For example, the pharmaceutical composition for preventing or treating diabetes mellitus may be dosed orally or parenterally.

A dosage of the pharmaceutical composition for preventing or treating diabetes mellitus according to the present disclosure may be appropriately selected by a person skilled in the art in consideration of an administration method, a user's age, sex and weight, and a severity of disease. For example, the dosage of the pharmaceutical composition for preventing or treating diabetes mellitus according to the present disclosure may be in a range of 0.0001 mg/kg to 1000 mg/kg, more preferably, 0.01 mg/kg to 100 mg/kg. The composition may be administered once a day, or may be administered several times a day. The dosage does not limit the scope of the present disclosure in any way.

Further, the pharmaceutical composition for preventing or treating diabetes mellitus according to the present disclosure may further contain a known compound or a plant extract having a blood glucose lowering activity in addition to the first composition. The pharmaceutical composition for preventing or treating diabetes mellitus according to the present disclosure may further contain the known compound or the plant extract having the blood glucose lowering activity in a content of 5 parts by weight to 20 parts by weight with respect to 100 parts by weight of the first composition.

The health functional food composition according to the present disclosure may be applied directly to animals including humans. The animal is a group of organisms that are distinguished from plants and mainly consumes organic matter as nutrients. Digestion, excretion and respiratory organs are differentiated in the animal. Preferably, the animal may be a vertebrate, more preferably a mammal. The mammal may preferably be a human.

The health functional food to which the composition according to the present disclosure may be added may include, for example, various foods, beverages, gum, candy, tea, vitamin complexes, and functional foods. In addition, in accordance with the present disclosure, the foods may include special nutritional foods (e.g., formulas, infants, baby foods, etc.), processed meat products, fish products, tofu, jellied foods, noodles (e.g., ramens, noodles, etc.), health supplement food, seasoned foods (e.g. soy sauce, miso, red pepper paste, mixed sauce, etc.), sauces, confectionery (e.g., snacks), dairy products (e.g. fermented milk, cheese, etc.), other processed food, kimchi, pickled food (various kimchi, pickles, etc.), drinks (e.g. fruits, vegetable drinks, soy milk, fermented drinks, ice cream, etc.), natural seasonings (e.g., ramen soup, etc.), vitamin complexes, alcoholic beverages, alcohols and other health supplement foods. However, the present disclosure is not limited thereto. The food, beverage or food additives may be prepared by conventional preparation methods.

In the present disclosure, the health functional food refers to a food group that provides an added value to act and express the function of the food for a special purpose via application of physical, biochemical, or biotechnological techniques, etc. to a food, or refers to a food that is designed and processed to allow body control functions of a food composition, such as bio-defense rhythm control, disease prevention and disease recovery to be realized sufficiently in the body. Preferably, the health functional food according to the present disclosure means a food capable of sufficiently expressing a bioregulatory function for preventing or ameliorating or diabetes mellitus and for lowering a blood glucose level in a living body. Further, the health functional food according to the present disclosure may mean a food that may exhibit an antioxidant effect. The health functional food may contain food additives that are food-acceptable. The food additives may further include suitable carriers, excipients and diluents commonly used in preparation of the health functional food.

When the *Lactobacillus plantarum* MG4229 strain according to the present disclosure is used in the quasi-drug composition, the strain, the culture medium or the cell-free supernatant of the strain may be added as it is or may be combined with other quasi-drug components, and may be suitably used according to conventional methods. A mixing amount of the active ingredient may be appropriately determined according to purposes of use (prevention, health, or therapeutic treatment) thereof.

Preferably, the quasi-drug composition may include a disinfecting cleaner, shower foam, gargling agent, wet tissue, detergent soap, hand wash, humidifier filler, mask, ointment or filter filler.

Further, the present disclosure provides a method for preventing or treating diabetes mellitus, the method comprising administering, to a subject, an effective dose of the *Lactobacillus plantarum* MG4229 strain (Accession No. KCTC13854BP).

Duplicate contents are omitted considering the complexity of the present specification of the application.

Terms not otherwise defined herein have meanings commonly used in the technical field to which the present disclosure belongs.

Hereinafter, the present disclosure will be described in detail based on Examples. However, the following Example are only to illustrate the present disclosure, and the present disclosure is not limited to the following Examples.

Example 1. Screening of α-Glucosidase Enzyme Activity Inhibition Effect of Lactic Acid Bacteria (LAB) Strain 1.1 Preparation of Sample for Screening of α-Glucosidase Enzyme Activity Inhibition Effect The lactic acid bacteria (LAB) strain was supplied from the Mediogen Co. Ltd located in Chungju, Korea. A total of 237 lactic acid bacteria (LAB) strains were used. Lactic acid bacteria (LAB) strain samples were prepared to evaluate activity inhibitory effect of α-glucosidase and α-amylase enzymes of these lactic acid bacteria (LAB) strains. After inoculating the lactic acid bacteria (LAB) strains into an MRS medium, the LAB strains were cultured at 37° C. for 15 hours and then resulting culture mediums were centrifuged (2,700 rpm, 15 minutes, 4° C.), and then supernatants thereof were filtered through a 0.2 μm syringe filter. Each of the filtered culture supernatants (cell free supernatant: CFS) was used as each sample.

1.2 Screening Experiment of α-Glucosidase Enzyme Activity Inhibition Effect

Specifically, the screening experiment was performed in a following manner. 150 μL of 0.01 M PBS (pH 7.0), 0.02 M p-nitrophenyl α-D-glucopyranoside (PNPG, Sigma-Aldrich Chemical Co., St, Louis, Mo., USA) 75 μL and lactic acid bacteria (LAB) culture supernatant (CFS) 25 μL were mixed with each other and then the mixture was incubated at 37° C. for 10 minutes. Thereafter, 50 μL of α-glucosidase (Sigma-Aldrich Chemical Co., St, Louis, Mo., USA) at 0.17 units/mL diluted using PBS was added thereto, followed by incubation at 37° C. for 10 minutes. A reaction was terminated by adding 1 mL of 0.1 M $Na_2CO_3$ to the culture medium. An amount of released p-nitrophenol (PNP) was measured based on absorbance at 405 nm. The inhibition of the enzyme activity was calculated based on a following Equation.

$$\text{Inhibition (\%)}=[1-(C-D)/(A-B)]\times 100$$

A: absorbance of α-glucosidase added and lactic acid bacteria (LAB) supernatant non-treated group B: absorbance of α-glucosidase non-added and lactic acid bacteria (LAB) supernatant non-treated group C: absorbance of α-glucosidase added and lactic acid bacteria (LAB) supernatant treated group D: absorbance of α-glucosidase non-added and lactic acid bacteria (LAB) supernatant treated group α-glucosidase inhibitions of over 300 species of human-derived lactic acid bacteria (LAB) obtained using the Equation were compared with each other. Based on the comparison result, 70 types of *Lactobacillus plantarum* (*L. plantarum*) strains and 36 types of *Lactobacillus paracasei* (*L. paracasei*) strains with excellent α-glucosidase inhibition were selected. Table 1 shows the selected *Lactobacillus plantarum* strains, and Table 2 shows the selected *Lactobacillus paracasei* strains.

TABLE 1

| | Sample | Inhibition (%) |
|---|---|---|
| 1 | MG4296 | 90.5754 ± 1.5809 |
| 2 | MG4229 | 79.0742 ± 5.9745 |
| 3 | MG5025 | 77.2505 ± 0.2527 |
| 4 | MG5144 | 69.5977 ± 3.1188 |
| 5 | MG4306 | 66.0562 ± 4.3720 |
| 6 | MG5145 | 61.6746 ± 1.4436 |
| 7 | MG5182 | 61.6222 ± 6.0654 |

TABLE 1-continued

| | Sample | Inhibition (%) |
|---|---|---|
| 8 | MG5013 | 56.4646 ± 5.3135 |
| 9 | MG5005 | 56.2815 ± 7.9072 |
| 10 | MG4228 | 54.1650 ± 4.9365 |
| 11 | MG4270 | 53.9667 ± 0.6976 |
| 12 | MG5106 | 52.6102 ± 1.1640 |
| 13 | MG4220 | 52.0 ± 6.3304 |
| 14 | MG5143 | 51.8315 ± 7.2569 |
| 15 | MG4219 | 51.0549 ± 4.3321 |
| 16 | MG4218 | 50.8150 ± 2.0709 |
| 17 | MG4214 | 49.2491 ± 3.2839 |
| 18 | MG5023 | 48.8600 ± 5.4469 |
| 19 | MG4234 | 48.0727 ± 6.8306 |
| 20 | MG5026 | 46.3913 ± 3.7521 |
| 21 | MG4271 | 45.7466 ± 5.8735 |
| 22 | MG5044 | 44.8960 ± 5.5175 |
| 23 | MG5107 | 44.0948 ± 1.3054 |
| 24 | MG5011 | 43.6361 ± 3.8271 |
| 25 | MG5034 | 41.8989 ± 3.8232 |
| 26 | MG4213 | 41.7296 ± 1.3163 |
| 27 | MG4058 | 41.4420 ± 2.7299 |
| 28 | MG5099 | 40.7134 ± 7.2096 |
| 29 | MG5141 | 38.7886 ± 4.6194 |
| 30 | MG5201 | 36.6252 ± 6.4439 |
| 31 | MG5087 | 33.7412 ± 7.4081 |
| 32 | MG5187 | 33.182 ± 3.2415 |
| 33 | MG5157 | 31.9482 ± 5.1898 |
| 34 | MG5080 | 31.9222 ± 16.8953 |
| 35 | MG4013 | 31.2530 ± 6.0539 |
| 36 | MG5070 | 30.8782 ± 4.3122 |
| 37 | MG5071 | 30.8110 ± 4.0954 |
| 38 | MG5155 | 29.9725 ± 1.5683 |
| 39 | MG5089 | 29.9146 ± 19.2226 |
| 40 | MG5041 | 29.5869 ± 4.0471 |
| 41 | MG4221 | 28.6490 ± 0.1358 |
| 42 | MG5255 | 27.9055 ± 5.1553 |
| 43 | MG5120 | 27.9037 ± 2.1870 |
| 44 | MG5188 | 25.795 ± 5.7214 |
| 45 | MG5142 | 25.2629 ± 2.3877 |
| 46 | MG5249 | 25.0679 ± 4.1434 |
| 47 | MG4237 | 25.0483 ± 7.6080 |
| 48 | MG5185 | 24.6339 ± 5.4633 |
| 49 | MG5122 | 23.6572 ± 2.9675 |
| 50 | MG5096 | 23.6218 ± 6.6304 |
| 51 | MG5197 | 22.7504 ± 9.5673 |
| 52 | MG5202 | 22.6398 ± 7.4367 |
| 53 | MG4215 | 22.2363 ± 0.3902 |
| 54 | MG5198 | 21.194 ± 6.2821 |
| 55 | MG4014 | 20.7704 ± 3.5719 |
| 56 | MG5251 | 20.0125 ± 1.2113 |
| 57 | MG5243 | 18.6025 ± 6.9193 |
| 58 | MG5247 | 17.2864 ± 2.0381 |
| 59 | MG5211 | 17.2816 ± 0.0535 |
| 60 | MG5102 | 17.1615 ± 1.4175 |
| 61 | MG4236 | 17.0185 ± 2.0734 |
| 62 | MG5204 | 16.3442 ± 2.5141 |
| 63 | MG5186 | 16.1036 ± 4.2115 |
| 64 | MG5248 | 14.3200 ± 4.2933 |
| 65 | MG5087 | 11.5183 ± 13.1659 |
| 66 | MG5203 | 11.2483 ± 2.1437 |
| 67 | MG4537 | 11.0528 ± 3.7077 |
| 68 | MG5254 | 10.0107 ± 3.7976 |
| 69 | MG207 | 7.1708 ± 2.6135 |
| 70 | MG5239 | 1.2740 ± 3.8531 |

TABLE 2

| | Sample | Inhibition (%) |
|---|---|---|
| 1 | MG5012 | 82.8178 ± 3.3793 |
| 2 | MG5004 | 70.7250 ± 2.2746 |
| 3 | MG5178 | 65.8054 ± 3.8249 |
| 4 | MG5172 | 62.5486 ± 8.0498 |
| 5 | MG5179 | 58.4315 ± 6.3360 |
| 6 | MG5163 | 54.9965 ± 4.3136 |

TABLE 2-continued

| | Sample | Inhibition (%) |
|---|---|---|
| 7 | MG5176 | 53.1680 ± 3.3225 |
| 8 | MG5010 | 52.7670 ± 2.6414 |
| 9 | MG5175 | 51.1778 ± 3.4339 |
| 10 | MG5146 | 47.5648 ± 1.4400 |
| 11 | MG4238-2 | 47.0389 ± 1.9221 |
| 12 | MG5135 | 46.2310 ± 1.4279 |
| 13 | MG5017 | 45.2574 ± 3.1768 |
| 14 | MG5190 | 43.901 ± 3.5751 |
| 15 | MG5009 | 43.5007 ± 5.2625 |
| 16 | MG5137 | 42.6829 ± 3.2563 |
| 17 | MG5132 | 41.6970 ± 2.8342 |
| 18 | MG5171 | 41.3421 ± 8.0605 |
| 19 | MG4267 | 40.4014 ± 6.5854 |
| 20 | MG5245 | 40.3593 ± 6.9539 |
| 21 | MG5148 | 40.3564 ± 2.5698 |
| 22 | MG5138 | 39.5842 ± 2.3523 |
| 23 | MG5103 | 38.3400 ± 2.4385 |
| 24 | MG5174 | 37.9740 ± 4.2575 |
| 25 | MG5015 | 35.9679 ± 1.0449 |
| 26 | MG5113 | 33.6986 ± 3.8943 |
| 27 | MG5016 | 31.3220 ± 5.9302 |
| 28 | MG5209 | 30.2657 ± 4.1541 |
| 29 | MG5173 | 27.1008 ± 3.7341 |
| 30 | MG5131 | 22.8305 ± 4.9142 |
| 31 | MG5189 | 22.0818 ± 2.9368 |
| 32 | MG5191 | 22.0267 ± 2.6416 |
| 33 | MG5101 | 20.8375 ± 6.9084 |
| 34 | MG5219 | 19.8705 ± 5.3 |
| 35 | MG5147 | 13.3142 ± 3.7356 |
| 36 | MG4272 | 11.7107 ± 5.3230 |

As shown in Table 1 and Table 2, MG4296, MG5012, and MG4229 strains were identified to exhibit superior α-glucosidase inhibitory activity, compared to other *L. plantarum* strains and *L. paracasei* strains. Thus, MG4296, MG5012, and MG4229 strains were identified to exhibit excellent α-glucosidase inhibitory activity among the lactic acid bacteria (LAB) strains.

Example 2. Measurement of Inhibition Effect of α-Amylase Enzyme Activity of Lactic Acid Bacteria (LAB) Strain Based on the measurement results of α-glucosidase inhibitory activity of Example 1, 30 types of lactic acid bacteria (LAB) strains, which exhibited excellent α-glucosidase inhibitory activity, were selected. An experiment was conducted to identify the α-amylase enzyme activity inhibition effect of the selected lactic acid bacteria (LAB) strain. Specifically, this experiment was performed in a following manner. 250 μL of α-amylase (Sigma-Aldrich Chemical Co., St, Louis, Mo., USA) solution (0.5 mg/mL) was mixed with 250 μL of the lactic acid bacteria (LAB) culture supernatant as prepared in the same manner as in Example 1.1 and then the mixture was reacted for 10 minutes 25° C. 250 μL of 1% starch solution in which starch (Samchun Pure Chemical Co. Ltd located in Pyeongtaek, Korea) was dissolved in a 0.02 M sodium phosphate buffer was added to the reaction solution, which in turn was further reacted at 25° C. for 10 minutes. Then, 500 μL of 96 mM 3,5-dinitrosalicylic acid (DNS, 30% sodium potassium tartrate in 0.5 M NaOH) (Sigma-Aldrich Chemical Co., St, Louis, Mo., USA) was added to the reaction solution to terminate the reaction. Then, the resulting reaction solution was boiled at 100° C. for 5 minutes to develop color, and was sufficiently cooled. Then, we added about 4 times of distilled water to the cooled reaction solution. Then, absorbance thereof was measured at 540 nm using ELISA (Spectra Max190, Molecular Devices, US). The inhibition of α-amylase enzyme activity was calculated based on a following Equation.

Inhibition (%)=[(A−B)/A]×100,

A: absorbance of lactic acid bacteria (LAB) supernatant non-treated group
B: absorbance of lactic acid bacteria (LAB) supernatant treated group α-amylase inhibitions of the 30 types of lactic acid bacteria (LAB) strains selected in Example 1 calculated based on the above Equation were compared and with each other and the results are shown in Table 3.

TABLE 3

| | Strains | Inhibition (%) |
|---|---|---|
| 1 | MG4270 | 81.05 ± 0.78 |
| 2 | MG5212 | 76.84 ± 0.47 |
| 3 | MG4062 | 82.12 ± 0.21 |
| 4 | MG4201 | 86.86 ± 0.44 |
| 5 | MG4202 | 86.57 ± 0.16 |
| 6 | MG4209 | 86.45 ± 0.54 |
| 7 | MG4428 | 64.91 ± 0.06 |
| 8 | MG4229 | 85.59 ± 0.65 |
| 9 | MG4283 | 86.11 ± 0.08 |
| 10 | MG5127 | 87.66 ± 0.21 |
| 11 | MG4290 | 86.64 ± 0.50 |
| 12 | MG4294 | 88.72 ± 0.55 |
| 13 | MG4295 | 83.68 ± 1.50 |
| 14 | MG4296 | 86.20 ± 0.36 |
| 15 | MG4298 | 82.71 ± 0.32 |
| 16 | MG4302 | 81.69 ± 0.38 |
| 17 | MG4306 | 57.01 ± 1.27 |
| 18 | MG5004 | 76.27 ± 0.57 |
| 19 | MG5012 | 87.36 ± 0.14 |
| 20 | MG5025 | 85.36 ± 0.15 |
| 21 | MG5144 | 83.22 ± 0.09 |
| 22 | MG5145 | 86.71 ± 0.10 |
| 23 | MG5162 | 88.21 ± 1.00 |
| 24 | MG5172 | 65.59 ± 2.78 |
| 25 | MG5178 | 79.72 ± 0.79 |
| 26 | MG5182 | 79.01 ± 0.03 |
| 27 | MG4501 | 62.62 ± 2.03 |
| 28 | MG4502 | 62.16 ± 0.68 |
| 29 | MG5126 | 85.49 ± 0.21 |
| 30 | MG4238-1 | 84.69 ± 0.81 |
| | Average | 81.24 |

As shown in Table 3, MG4296 strain, MG4229 strain and MG5012 strain were identified as having α-amylase inhibition values higher than an average value of the α-amylase inhibitions of the 30 strains. Therefore, MG4229 strain, MG4296 strain and MG5012 strain were identified as having excellent α-amylase inhibition.

Example 3. Measurement of Antioxidant Activity of Lactic Acid Bacteria (LAB) Strain 3.1 Preparation of Sample for Measuring Antioxidant Activity of Lactic Acid Bacteria (LAB) Strain Samples used to measure antioxidant activity were prepared according to a following method. We inoculated the lactic acid bacteria (LAB) strains into MRS medium and cultured the strains therein at 37° C. for 18 hours. Then, each culture medium was centrifuged (7,000×g, 20 min, 4° C.) to collect a pellet (intact cell, IC), which in turn was washed using PBS three times and then was resuspended in PBS. The resulting IC was used as an IC sample. Moreover, intracellular cell-free extract (ICFE) was washed twice with deionized water and then ultrasonically crushed for 10 minutes, followed by centrifugation (10,000×g, 10 minutes, 4° C.). Thus, a supernatant was collected and filtered through a 0.2 μm syringe filter and then was used as an ICFE sample.

3.2 Measurement of Antioxidant Activity of Lactic Acid Bacteria (LAB) Strain

The antioxidant activity of the 30 types of lactic acid bacteria (LAB) strains which exhibited excellent α-glucosidase inhibitory activity was identified based on measuring results of DPPH radical scavenging ability and ABTS radical scavenging ability. Each test method is as follows.

3.2.1. DPPH Radical Scavenging Ability Measurement

DPPH radical scavenging ability was measured according to Lim's method. Specifically, we added 100 μL of IC (intact cell) or ICFE (intracellular cell-free extract) sample as prepared in Example 3.1 to each 96-well plate. Then, we added 100 μL of 0.4 mM DPPH solution thereto. Then, light was blocked, and a reaction thereof occurred at 20° C. for 30 minutes. Then, an absorbance of the reaction solution was measured at 540 nm using a microplate reader. The DPPH radical scavenging ability was calculated based on a following Equation.

DPPH radical scavenging ability (%)=1−(experimental group absorbance/control group absorbance)×100

3.2.2. ABTS Radical Scavenging Ability Measurement

ABTS radical scavenging ability was measured based on modification of the method disclosed by Re et al. Specifically, a reaction mixture between 7.4 mM ABTS and 2.6 mM potassium persulfate was left at room temperature in a dark place for 24 hours. The radical-formed reaction solution was diluted with PBS such that the absorbance reached 0.700±0.03 at 732 nm. The IC (intact cell) or ICFE (intracellular cell-free extract) sample as prepared in Example 3.1 was loaded into 96-well plates with 20 μL and 180 μL of ABTS solutions, respectively, and then incubated therein for 10 minutes while blocking light. An absorbance of the reaction solution was measured at 732 nm using a microplate reader. The ABTS radical scavenging ability was calculated based on a following Equation.

ABTS radical scavenging ability activity (%)=[1−(A−B)/C]×100,

A: absorbance of sample treated group
B: absorbance of PBS and sample treated group
C: absorbance of sample untreated group Based on the DPPH radical scavenging ability and ABTS radical scavenging ability, the antioxidant ability of the 30 types of lactic acid bacteria (LAB) strains that exhibited the excellent α-glucosidase inhibitory activity was measured. Table 4 shows an antioxidant activity value of the MG4229 strain and an average value of antioxidant activity values of the 30 types of lactic acid bacteria (LAB) strains.

TABLE 4

| | DPPH scarvenging (%) | | ABTS scavenging (%) | |
|---|---|---|---|---|
| Strains | IC | ICFE | IC | ICFE |
| MG4229 | 63.4 ± 0.9 | 14.6 ± 0.5 | 53.4 ± 1.3 | 25.4 ± 0.3 |
| Average of 30 LABs | 50.5 | 12.9 | 50 | 28.4 |

IC: Intact cells;
ICFE: Intracellular Cell-Free Extract

As shown in Table 4, the DPPH radical scavenging ability of the MG4229 strain was 63.4% in the IC sample and 14.6% in the ICFE sample. The ABTS radical scavenging ability thereof was 53.4% in the IC sample. This indicate that the MG4229 strain has superior antioxidant ability than the average antioxidant ability of the 30 types of lactic acid bacteria (LAB) strains. That is, it was identified that the MG4229 strain has the excellent α-glucosidase inhibitory activity and, at the same time, the excellent antioxidant activity.

Example 4. Identification of MG4229, MG4296 and MG5012 Strains 4.1 Nucleic Acid Sequence Analysis and Phylogenetic Tree Identification of MG4229, MG4296 and MG5012 Strains 16S rRNA gene nucleic acid sequence analysis using universal rRNA gene primers (27F, 1492R) of MG4229, MG4296 and MG5012 strains was conducted and identified. Each process was performed by Sol-gent (Daejeon, Korea). The analyzed nucleic acid sequences were compared with the Genebank database using the Basic Local Alignment Search Tool (Blast) of the National Center for Biotechnology Institute (NCBI) and were identified based on the comparison results. Phylogenetic trees were prepared using a neighbor joining method of a MEGA 7.0 software. The analyzed 16s rRNA nucleic acid sequence of the MG4229 strain was expressed as SEQ ID NO: 1. The phylogenetic tree of MG4229, MG4296 and MG5012 strains is shown in FIG. 1.

Figure 1:
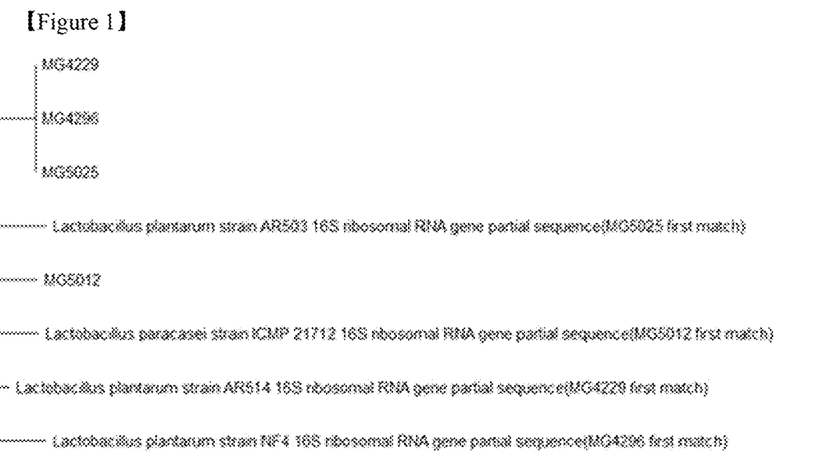
FIG. 1 is a diagram showing a systematic diagram of a MG4229 strain.

As shown in FIG. 1, based on the analysis result of the nucleic acid sequence, the strains with excellent α-glucosidase and α-amylase inhibitory activity were identified as *Lactobacillus plantarum* MG4229, *Lactobacillus plantarum* MG4296, and *Lactobacillus paracasei* MG5012. The identified *Lactobacillus plantarum* MG4229 was deposited on Jun. 4, 2019 into Korean collection for type culture, Korea and was assigned an accession number KCTC13854BP.

Example 5. Measurement of Glucose Tolerance of MG4229 Strain

Figure 2:
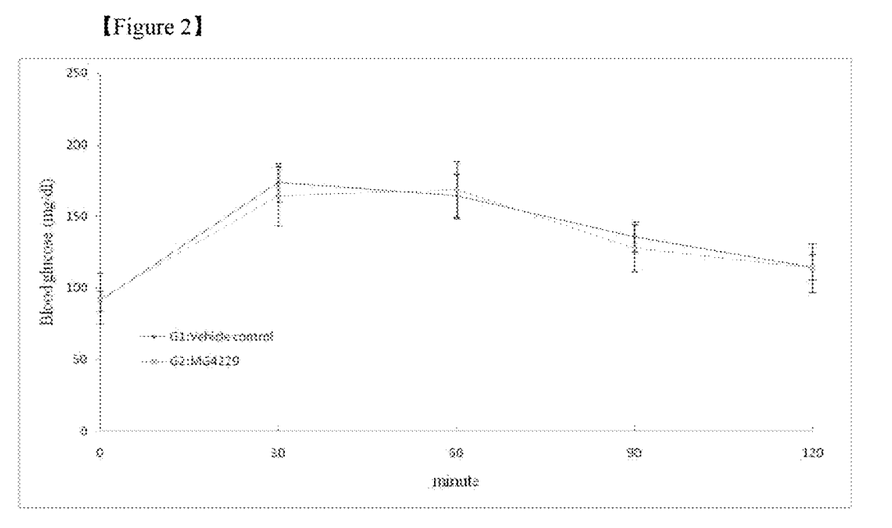
FIG. 2 is a diagram showing a blood glucose curve for measuring a glucose tolerance of the MG4229 strain.

An oral glucose tolerance test was performed to identify the glucose tolerance in an animal model of the lactic acid bacteria (LAB) MG4229, which exhibited excellent antioxidant activity and α-glucosidase enzyme activity inhibitory activity. Specifically, MG4229 lactic acid bacteria (LAB) was set as an experimental group. A control group was set as an excipient treated group. We dissolved lactic acid bacteria (LAB) in 200 μl PBS and orally administered the solution ($1\times10^8$ CFU/mouse) to an ICR mouse fasted for 16 hours. After 1 hour, 2 g/kg of glucose was administered orally thereto, and then the blood glucose was measured using a blood glucose meter (ACCU-CHEK®Performa, Roche Diagnostics, Mannheim, Germany) in 30 minutes, 60 minutes, 90 minutes and 120 minutes. FIG. 2 shows the results of blood glucose measurement.

As shown in FIG. 2, it was identified that the increase in the blood glucose after administration of the glucose to the MG4229 treated group was slower than that in the control group. Therefore, the administration of the novel lactic acid bacteria (LAB) strain MG4229 delays the absorption of sugars. Thus, the novel lactic acid bacteria (LAB) strain MG4229 was identified as a lactic acid bacteria (LAB) strain that has a blood glucose-lowering effect and may help increase the sugar tolerance.

Example 6. Identification of Improvement Effect of Insulin Resistance of MG4229 Strain We determined whether the insulin resistance is improved based on measuring results of glucose consumption rate in a mouse 3T3-L1 cell line as an adipocyte cell line. The adipose cells 3T3-L1 was differentiated with MDI differentiation inducing solution, and then treated with glucose 1 mg/ml and MG4229 strain extract (CFE), respectively. Then, we quantified an amount of glucose content consumed during the cell culture using a kit. A specific experimental method is as follows.

6.1 Preparation of Lactic Acid Bacteria (LAB) Extract (CFE)

After inoculating the MG4229 strain into MRS medium and culturing the strain at 37° C. for 15 hours, we centrifuged the culture medium (2,700 rpm, 15 minutes, 4° C.) to collect a strain pellet which in turn was washed twice with PBS. The washed strain was lyophilized, then resuspended in PBS and the suspension was filtered through a 0.2 μm syringe filter. The filtered lactic acid bacteria (LAB) extract (cell free extract: CFE) was used as a sample. The number of lactic acid bacteria (LAB) was adapted to a concentration of $1\times10^8$ or $2\times10^8$ CFU/ml.

6.2 Measurement of Insulin Resistance Improvement Effect of MG4229 Strain

As control groups, a group not treated with the MDI differentiation-inducing substance and untreated with the lactic acid bacteria (LAB) extract, and a group treated with the MDI-differentiation-inducing substance and non-treated with the lactic acid bacteria (LAB) extract were used. As an experimental group, a group treated with both of the MDI differentiation inducer and the MG4229 lactic acid bacteria (LAB) extract prepared in Example 6.1 was used. The experimental method was conducted as follows. The 3T3-L1 cell was cultured using DMEM containing 10% FBS, and then seeded to a 6-well plate at $3\times10^5$ cells/well and was cultured therein. The medium was exchanged with 10% FBS DMEM medium containing insulin (10 μg/mL) as a cell differentiation inducing substance (MDI), dexamethasone (1 μM), 3-isobutyl-1-methylxanthine (0.5 mM), and the sample. Then, the cell was cultured therein for 2 days. After the 2 days, the previous medium were exchanged with 10% FBS DMEM medium containing only the sample and the insulin (10 μg/mL) and the cell was cultured therein for 2 days. In order to stabilize the cells, the previous medium was exchanged with 10% FBS DMEM medium and the cell was cultured for 2 days. After incubation for 2 days, the previous medium was replaced with glucose-free DMEM medium containing 10% FBS, 1% sodium pyruvate, and antibiotics. 1 mg/ml of glucose was injected to the medium for all of the experimental groups. The cell was cultured for 2 days. After culturing for the 2 days, the culture medium was centrifuged at 1,000 rpm for 5 minutes to remove cells present in the culture medium. At this time, the culture medium was stored at −80° C. until measurement. A glucose content in the differentiation-induced 3T3-L1 cell medium was quantified using a glucose assay kit (GAGO-20, Sigma-Aldrich Co., Ltd). The quantitative results are shown in FIG. 3.

Figure 3:
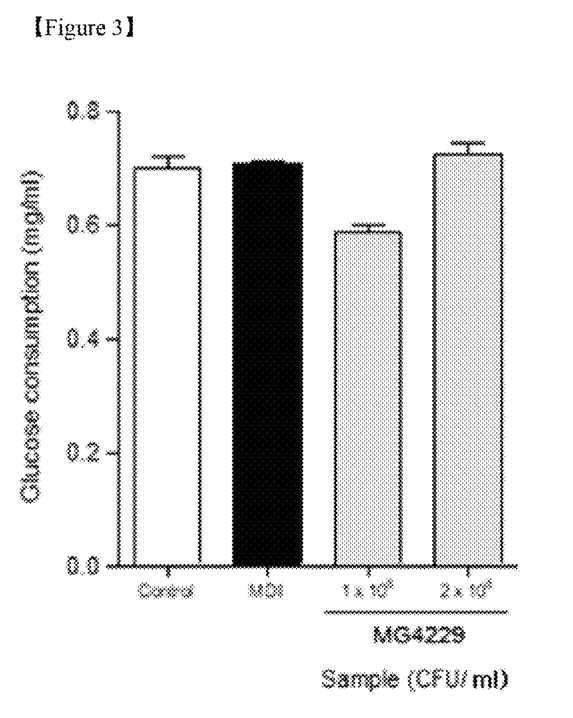
FIG. 3 is a graph measuring a glucose consumption of 3T3-L1 cells according to treatment thereof with the MG4229 strain to measure an effect of improving an insulin resistance of the MG4229 strain.

As shown in FIG. 3, based on a result of comparing the glucose consumptions of the MDI differentiation-inducing substance treated and lactic acid bacteria (LAB) extract untreated group and the MG4229 lactic acid bacteria (LAB) extract treated group, it was identified that as the injected amount of the lactic acid bacteria (LAB) bacteria increased, the consumption of glucose increased. The increase in the glucose consumption means that the insulin resistance of the cell is improved, and thus the influx of glucose into the cell is increased. Therefore, it was identified that the MG4229 strain improved the insulin resistance in a dose dependent manner.

Example 7. Identification of Acid Tolerance and Bile Tolerance of MG4229 Strain An experiment was conducted to identify viability of the MG4229 strain against acid and bile salt as in the intestinal environment.

7.1 Identification Experiment of Acid Tolerance of MG4229 Strain

The experiment to identify the acid tolerance of the lactic acid bacteria (LAB) MG4229 strain according to the present disclosure was conducted as follows. The MG4229 strain was streaked on an MRS plate medium and incubated at 37° C. for 24 hours, and then the resulting colonies were inoculated into a MRS liquid medium and cultured (37° C., 18 hours). Thereafter, the culture medium was centrifuged (4000×g, 4° C., 5 minutes), and then washed twice with phosphate-buffer saline (PBS, pH 7.4). A concentration of the washed cells was adjusted to $OD_{600}$ 1.0 ($10^1$-$10^9$ CFU/mL) to prepare a diluted lactic acid bacteria (LAB) solution. After adding 1 ml of the diluted lactic acid bacteria (LAB) solution to 9 ml PBS of pH 2 or pH 7, the mixture was shaken and was incubated at 37° C. for 3 hours. Then, the viable cell count was identified. Table 5 shows the results of viable cell counting.

TABLE 5

|  | pH tolerance | |
| --- | --- | --- |
| Selected strain | pH7 | pH2 |
| MG4229 | 8.57 ± 0.26 | 5.25 ± 0.26 |

As shown in Table 5, it was identified that the MG4229 strain maintains a viable cell count of $10^4$ CFU/mL or higher after 3 hours at pH 2. In general, the lactic acid bacteria (LAB) is determined to have excellent acid tolerance when maintaining a viable cell count of $10^4$ CFU/mL or higher for 3 hours at pH 2. Thus, the MG4229 strain according to the present disclosure was identified as having excellent acid tolerance.

7.2 Identification Experiment of Bile Tolerance of MG4229 Strain

To identify the resistance of the MG4229 strain to a bile salt, we inoculated 1% of the diluted lactic acid bacteria (LAB) solution as prepared in Example 7.1 into MRS medium containing 1% to 3% oxgall. After incubation of the mixture at 37° C. for 24 hours, the viable cell count was identified. Table 6 shows the results.

TABLE 6

|  | Bile salt tolerance (Log CFU/mL) | | | |
| --- | --- | --- | --- | --- |
| Selected strain | 0% | 0.1% | 0.3% | 0.5% |
| MG4229 | 9.16 ± 0.11 | 8.59 ± 0.09 | 7.85 ± 0.10 | 7.79 ± 0.03 |

As shown in Table 6, it was identified that the MG4229 strain maintains remarkably high viable cell counts of 6.86 log CFU/mL and 7.41 log CFU/mL, respectively, at 0.5% bile salt concentration. Generally, to identify resistance to the bile salt, the resistance is identified at a concentration of 0.3% of the bile salt. It is known according to existing research results that the LAB strain is sensitive to the bile salt when the viable cell count of lactic acid bacteria (LAB) in the 0.3% bile salt is lower than 4 log CFU/mL. Thus, the MG4229 strain maintains the number of viable cells higher than 4 log CFU/mL at higher concentrations of the bile salt, and thus has excellent bile tolerance.

Example 8. Identification of Intestinal Adhesion MG4229 Strain

The auto-aggregation and hydrophobicity indirectly indicate the adhesion of microorganisms to epithelial cells. According to a study by Kos, it is known that strains with high auto-aggregation and high hydrophobicity on the surface of the cell are higher adhesion to actual cells.

8.1 Identification of Auto-Aggregation of MG4229 Strain

In order to indirectly identify the adhesion of the strain to the intestinal cells, Kassa's study was modified to conduct an auto-aggregation experiment. The lactic acid bacteria (LAB) culture medium cultured in MRS medium for 18 hours was inoculated in a new 10 mL MRS medium in a content of 2%, and was cultured for 18 hours and was used in the experiment. The cultured lactic acid bacteria (LAB) were centrifuged (4,000×g, 4° C., 5 minutes), and washed twice in PBS. A concentration of the cells was adjusted to $OD_{600}$ 1.0. The strain suspension was shaken 5 mL for 10 seconds. Then, immediately after the start of the experiment (AO) and after 1, 3 or 5 hours for which the suspension was left (A), 0.1 mL of supernatant was taken and mixed with 0.9 mL PBS. Then, an absorbance of the mixture was measured at 600 nm. The auto-aggregation percentage was calculated according to a following Equation. Table 7 shows the results.

$$Autoaggregation\ (\%) = \frac{(A0 - A)}{A0} \times 100$$

TABLE 7

|  | Autoaggregation (%) | | |
| --- | --- | --- | --- |
|  | 1 h | 3 h | 5 h |
| MG4229 | 23.5 | 38.7 | 70.1 |

As shown in Table 7, the auto-aggregation of the strain was 70.1% when the MG4229 strain suspension was left for 5 hours. According to a study by Malik, when the in vitro auto-aggregation of L. Plantarum CMPG5300 was about 67%, adhesion to the vaginal epithelial cells was higher than 50%. Thus, the strain having the high auto-aggregation exhibited excellent ability to form biofilms on the cell surface. Based on the above study, considering that the auto-aggregations of the 8 strains other than the L. plantarum CMPG5300 were lower than 20,%, the auto-aggregation of the MG4229 strain was identified to be excellent.

8.2 Identification of Hydrophobicity of MG4229 Strain

For indirectly identifying adhesion to intestinal cells, hydrophobicity was identified based on modification of a MATS (microbial adhesion to solvents) test method related to solvents of KOS. The MG4229 strain was cultured in MRS medium (37° C. for 18 hours), and centrifuged (4,000× g, 4° C., 15 minutes) and washed twice in PBS. The cells were suspended at $OD_6$1.0 (AO) using PBS. We dispensed 3 mL of the suspension into 1 mL of xylene, chloroform, and ethylacetate respectively. Each test tube was shaken for 1 minute and then left at room temperature for 5 minutes. Then, an aqueous solution was collected and an absorbance thereof was measured (A) at 600 nm. The adhesion to the solution was calculated according to a following Equation. Table 8 shows the results.

$$\text{Adhesion rate (\%)} = \frac{(A0 - A)}{A0} \times 100$$

TABLE 8

| | Hydrophobicity (%) | | |
|---|---|---|---|
| | Xylene | Chloroform | Ethyl acetate |
| MG4229 | 66.7 | 62.3 | 14.3 |

As shown in Table 8, regarding the adhesion of the strain to the xylene which indicates the hydrophobicity to the cells, the MG4229 strain exhibited a high hydrophobicity of 66.7%. The hydrophobicity to the cell surface means presence of protein on the cell surface. The hydrophilic characteristics to the cell surface means presence of a lot of polysaccharides. The more the proteins, the better the auto-aggregation and the adhesion to cells. The strain with excellent adhesion to the cell may prevent infection by settling on the cells, thereby inhibiting adhesion of pathogens to the cells. In this connection, the MG4229 strain was identified to have high adhesion to the epithelial cell in the intestine based on the high auto-aggregation and adhesion to the xylene. Thus, it was identified that the MG4229 strain may adhere to the intestine to stably maintain the blood glucose lowering effect.

Further, as shown in Table 8, based on a result of identification of adhesion to chloroform and ethyl acetate as conducted to identify cell surface properties, the MG4229 strain exhibited higher adhesion to the acidic solvent chloroform (electroreceptor). Thus, it was identified that the MG4229 strain contained an electron donor with the cell surface.

Example 9. Antibiotic Susceptibility Test of MG4229 Strain

Antibiotic susceptibility experiments of MG4229 strain were performed using a BHI (Brain Heart Infusion Agar) plate medium, based on the Clinical and Laboratory Standard Institute (CLSI) guidelines. The MG4229 strain was inoculated into 1% in MRS medium, cultured for 18 hours, and then the culture medium was centrifuged (4,000×g, 4° C., 5 minutes), and then washed twice in PBS. Then, a turbidity of the strain solution was adjusted to McFarland turbidity standard 0.5, and the strain was applied to the BHI plate medium using a sterile cotton swab. After the medium was dried, an antibiotic disk was placed on the medium coated with the bacterial solution and then the strain was cultured at 37° C. for 24 hours. A size of the resulting inhibitory ring was measured in mm. The antibiotic susceptibility experiments of MG4229 strain was classified into three levels such as the sensitive, intermediate, and resistant levels according to a standard indicator. The antibiotics as used were ampicillin (10 μg), gentamicin (10 μg), kanamycin (30 μg), streptomycin (10 μg), tetracycline (30 μg), erythromycin (15 μg), vancomycin (30 μg), chloramphenicol (30 μg), and clindamycin (2 μg). The results are shown in Table 9.

TABLE 9

| Antibiotics (μg/disc) | MG4229 | Antibiotics (μg/disc) | MG4229 |
|---|---|---|---|
| ampicillin (10) | S | erythromycin (15) | S |
| vancomycin (30) | R | clindamycin (2) | R |
| gentamycin (10) | S | teracycline (30) | S |
| kanamycin (30) | R | chloramphenicol (30) | S |
| streptomycin (10) | S | | |

As shown in Table 9, it was identified that the MG4229 exhibited resistance to vancomycin, kanamycin, and clindamycin, and exhibited antibiotic susceptibility to ampicillin, gentamicin, streptomycin, erythromycin, tetracycline, and chloramphenicol.

Example 10. Measurement of Enzyme Activity of MG4229 Strain

The MG4229 strain was streaked on the MRS plate medium and incubated at 37° C. for 24 hours, and then the resulting colonies were inoculated into the MRS liquid medium, followed by stationary culture (37° C., 18 hours). Afterwards, the culture medium was centrifuged (4000×g, 4° C. 5 minutes), and then washed twice with phosphate-buffer saline (PBS, pH 7.4). A turbidity of the washed cells was adjusted to 5 to 6 McFarland using 2 mL of suspension medium (BioMerieux, France) for the test. The bacterial solution was dispensed into a tube of an API ZYM strip, incubated at 37° C. for 4 hours, and then a drop of each of ZYM A and ZYM B reagents (BioMerieux, France) was added thereto. After 10 minutes, enzyme activity was identified based on color change. Table 10 shows the enzyme activity results.

TABLE 10

| Enzyme | MG4229 |
|---|---|
| Alkaline phosphatase | — |
| Esterase [C4] | 1 |
| Esterase Lipase [C8] | 1 |
| Lipase [C14] | 1 |
| Leucine arylamidase | 1 |
| Valine arylamidase | 5 |
| Crystinearylamidase | 4 |
| Trypsin | 1 |
| α-chymotrypsin | 1 |
| Acid phosphatase | 1 |
| Naphtol-AS-BI-phosphohydrolase | 3 |
| α-galactosidase | 2 |
| β-glucuronidase | 1 |
| β-glucosidase | 5 |
| α-glucosidase | — |
| bet-glucosidase | 3 |
| N-acetyl-beta-glucosaminidase | 4 |
| α-mannosidase | 3 |
| α-fucosidase | — |

As shown in Table 10, the MG4229 strain induces enzyme activity of esterase (C4), esterase lipase (C8), lipase (14), leucine arylamidase, valine arylamidase, crystinearylamidase, trypsin, α-chymotrypsin, acid phosphatase, naphtol-AS-BI-phosphohydrolase, α-galactosidase, β-glucuronidase, β-glucosidase, n-acetyl-β-glucosaminidase, or α-mannosidase.

Example 11. Identification of Fermentation Characteristics Per API of MG4229 Strain The MG4229 strain was streaked on the MRS plate medium and incubated at 37° C. for 24 hours, and then the resulting colonies were inoculated into the MRS liquid medium, followed by stationary culture (37° C., 18 hours). Then, the culture medium was centrifuged (4000×g, 4° C., 5 minutes), and then washed twice with phosphate-buffer saline (PBS, pH 7.4). A turbidity of the washed cells was adjusted to 2 McFarland using API 50CHL medium 10 mL (BioMerieux, France) for the test. The API50 CHL medium in which the bacteria were suspended was dispensed into a tube of the strip, and mineral oil was added thereto, to make the tube to be anaerobic. Then, the strain was incubated at 37° C. for 48 hours. Table 11 shows the results.

TABLE 11

| MG4229 | | | |
|---|---|---|---|
| Glycerol | − | Salicin | + |
| Erythritol | − | D-cellobiose | + |
| D-arabinose | − | D-maltose | + |
| L-arabinose | + | D-lactose | + |
| D-ribose | + | D-melibiose | + |
| D-xylose | − | D-saccharose | + |
| L-xylose | − | D-trehalose | + |
| D-adonitol | − | Inulin | − |
| Methyl-β D-xylopyranoside | − | D-melezitose | + |
| D-galactose | + | D-raffinose | + |
| D-glucose | + | Amidon | − |
| D-fructose | + | Glycogen | − |
| D-mannose | + | Xylitol | − |
| L-sorbose | − | Gentibiose | + |
| L-rhamnose | − | D-turanose | + |
| Dulcitol | − | D-lyxose | − |
| Inositol | − | D-tagatose | − |
| Mannitol | + | D-fucose | − |
| D-sorbitol | + | L-fucose | − |

TABLE 11-continued

| MG4229 | | | |
|---|---|---|---|
| Methyl α D-mannopyranoside | + | D-arabitol | − |
| Methyl α D-glucopyranoside | − | L-arabitol | − |
| N-acetylglucosamine | + | Potassium gluconate | + |
| Amygdalin | + | Potassium 2-ketogluconate | − |
| Arbutin | + | Potassium 5-ketogluconate | − |
| Esculin | + | | |

As shown in Table 11, the MG4229 strain exhibits fermentation characteristics of L-arabinose, D-ribose, D-galactose, D-glucose, D-fructose, D-mannose, mannitol, D-sorbitol, methyl α D-mannopyranoside, N-acetylglucosamine, amygdalin, arbutin, esculin, salicin. D-cellobiose. D-maltose, D-lactose, D-melibiose, D-saccharose, D-trehalose, D-melezitose, D-raffinose, gentibiose, D-turanose, or potassium gluconate.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

Accession Number

Depository name: Korea Research Institute of Bioscience and Biotechnology, 181 Ipsin-gil, Jeongeup-si., Jeollabuk-do56212, Republic of Korea Accession number: KCTC13854BP Date of Deposit: 20190604

What is claimed is:

1. A method for lowering a blood glucose level in a subject, the method comprising:
administering to the subject a composition comprising an effective dose of a *Lactobacillus plantarum* MG4229 strain (Accession No. KCTC13854BP) having blood glucose lowering activity and antioxidant activity, a conditioned culture medium by culturing of the strain, or a cell-free supernatant of the strain.

2. The method of claim 1, wherein the *Lactobacillus plantarum* MG4229 strain has α-glucosidase inhibitory activity.

3. The method of claim 1, wherein the *Lactobacillus plantarum* MG4229 strain has α-amylase inhibitory activity.

4. The method of claim 1, wherein the *Lactobacillus plantarum* MG4229 strain improves insulin resistance.

5. The method of claim 1, wherein the *Lactobacillus plantarum* MG4229 strain is stable in a range of pH 2 to pH 7.

6. The method of claim 1, wherein the *Lactobacillus plantarum* MG4229 strain is stable in a bile salt.

7. The method of claim 1, wherein the *Lactobacillus plantarum* MG4229 strain exhibits auto-aggregation.

8. The method of claim 1, wherein the *Lactobacillus plantarum* MG4229 strain has a hydrophobicity to a cell surface.

9. The method of claim 1, wherein the *Lactobacillus plantarum* MG4229 strain induces enzyme activity of esterase (C4), esterase lipase (C8), lipase (14), leucine arylamidase, valine arylamidase, crystinearylamidase, trypsin, α-chymotrypsin, acid phosphatase, naphtol-AS-BI-phosphohydrolase, α-galactosidase, β-glucuronidase, β-glucosidase, n-acetyl-β-glucosaminidase, or α-mannosidase.

10. The method of claim 1, wherein the *Lactobacillus plantarum* MG4229 strain exhibits fermentation characteristics of L-arabinose, D-ribose, D-galactose, D-glucose, D-fructose, D-mannose, mannitol, D-sorbitol, methyl α D-mannopyranoside, N-acetylglucosamine, amygdalin, arbutin, esculin, salicin, D-cellobiose, D-maltose, D-lactose, D-melibiose, D-saccharose, D-trehalose, D-melezitose, D-raffinose, gentibiose, D-turanose, or potassium gluconate.

11. The method of claim 1, wherein the *Lactobacillus plantarum* MG4229 strain has antibiotic resistant to vancomycin, kanamycin, and clindamycin.

12. The method of claim 1, wherein the composition is a health functional food composition or pharmaceutical composition.

13. A method for preventing, ameliorating, or treating diabetes mellitus, the method comprising administering, to a subject, an effective dose of a *Lactobacillus plantarum* MG4229 strain (Accession No. KCTC13854BP).

* * * * *

UNITED STATES PATENT AND TRADEMARK OFFICE
CERTIFICATE OF CORRECTION

PATENT NO. : 11,738,057 B2
APPLICATION NO. : 16/936211
DATED : August 29, 2023
INVENTOR(S) : Paek et al.

It is certified that error appears in the above-identified patent and that said Letters Patent is hereby corrected as shown below:

In the Specification

Column 13, Table 3: Please delete the table and replace with the following:

[Table 3]

| | Strains | Inhibition (%) | | Strains | Inhibition (%) |
|---|---|---|---|---|---|
| 1 | MG4270 | 81.05±0.78 | 16 | MG4302 | 81.69±0.38 |
| 2 | MG5212 | 76.84±0.47 | 17 | MG4306 | 57.01±1.27 |
| 3 | MG4062 | 82.12±0.21 | 18 | MG5004 | 76.27±0.57 |
| 4 | MG4201 | 86.86±0.44 | 19 | MG5012 | 87.36±0.14 |
| 5 | MG4202 | 86.57±0.16 | 20 | MG5025 | 85.36±0.15 |
| 6 | MG4209 | 86.45±0.54 | 21 | MG5144 | 83.22±0.09 |
| 7 | MG4228 | 84.91±0.06 | 22 | MG5145 | 86.71±0.10 |
| 8 | MG4229 | 85.59±0.65 | 23 | MG5162 | 88.21±1.00 |
| 9 | MG4283 | 86.11±0.08 | 24 | MG5172 | 65.59±2.78 |
| 10 | MG5127 | 87.66±0.21 | 25 | MG5178 | 79.72±0.79 |
| 11 | MG4290 | 86.64±0.50 | 26 | MG5182 | 79.01±0.03 |
| 12 | MG4294 | 88.72±0.55 | 27 | MG4501 | 62.62±2.03 |
| 13 | MG4295 | 83.68±1.50 | 28 | MG4502 | 62.16±0.68 |
| 14 | MG4296 | 86.20±0.36 | 29 | MG5126 | 85.49±0.21 |
| 15 | MG4298 | 82.71±0.32 | 30 | MG4238-1 | 84.69±0.81 |
| | Average | 81.24 | | | |

Column 17, Line 18: Please correct "($10'$-$10^9$ CFU/mL)" to read --($10^8$-$10^9$ CFU/mL)--

Signed and Sealed this
Thirty-first Day of October, 2023

Katherine Kelly Vidal
*Director of the United States Patent and Trademark Office*

CERTIFICATE OF CORRECTION (continued)
U.S. Pat. No. 11,738,057 B2

Column 18, Line 26: Please correct "(AO)" to read --(A0)--

Column 18, Line 63: Please correct "$OD_6$" to read --$OD_{600}$--

Column 18, Line 63: Please correct "(AO)" to read --(A0)--